/

US011382731B2

(12) United States Patent
Skalla et al.

(10) Patent No.: US 11,382,731 B2
(45) Date of Patent: Jul. 12, 2022

(54) MEDICAL DEVICES WITH SEALING PROPERTIES

(71) Applicant: Covidien LP, Mansfield, MA (US)

(72) Inventors: Walter Skalla, Old Lyme, CT (US); Lauren Vernlund, Berlin, CT (US)

(73) Assignee: Covidien LP, Mansfield, MA (US)

( * ) Notice: Subject to any disclaimer, the term of this patent is extended or adjusted under 35 U.S.C. 154(b) by 985 days.

(21) Appl. No.: 15/047,916

(22) Filed: Feb. 19, 2016

(65) Prior Publication Data

US 2016/0250013 A1   Sep. 1, 2016

Related U.S. Application Data

(60) Provisional application No. 62/121,831, filed on Feb. 27, 2015.

(51) Int. Cl.
| | |
|---|---|
| *A61F 2/00* | (2006.01) |
| *A61F 2/02* | (2006.01) |
| *A61B 17/072* | (2006.01) |
| *A61L 31/04* | (2006.01) |
| *A61L 31/10* | (2006.01) |
| *A61L 31/14* | (2006.01) |
| *A61B 17/04* | (2006.01) |
| *A61F 13/53* | (2006.01) |

(52) U.S. Cl.
CPC ...... *A61F 2/0063* (2013.01); *A61B 17/07292* (2013.01); *A61F 2/02* (2013.01); *A61L 31/042* (2013.01); *A61L 31/10* (2013.01); *A61L 31/146* (2013.01); *A61B 2017/0495* (2013.01); *A61F 2013/530043* (2013.01); *A61F 2210/00* (2013.01); *A61F 2240/00* (2013.01); *A61F 2310/00365* (2013.01)

(58) Field of Classification Search
CPC .... A61F 2/0063; A61F 2/02; A61B 17/07292; A61L 31/10; A61L 31/042; A61L 31/146
See application file for complete search history.

(56) References Cited

U.S. PATENT DOCUMENTS

| | | |
|---|---|---|
| 3,364,200 A | 1/1968 | Ashton et al. |
| 3,666,750 A | 5/1972 | Briskin et al. |
| 3,937,223 A | 2/1976 | Roth |
| 4,511,478 A | 4/1985 | Nowinski et al. |
| 4,626,253 A | 12/1986 | Broadnax, Jr. |
| 4,663,163 A | 5/1987 | Hou et al. |
| 4,826,945 A | 5/1989 | Cohn et al. |
| 4,938,763 A | 7/1990 | Dunn et al. |
| 5,100,992 A | 3/1992 | Cohn et al. |
| 5,160,745 A | 11/1992 | DeLuca et al. |
| 5,201,745 A | 4/1993 | Tayot et al. |
| 5,306,500 A | 4/1994 | Rhee et al. |
| 5,410,016 A | 4/1995 | Hubbell et al. |
| 5,484,913 A | 1/1996 | Stilwell et al. |
| 5,505,952 A | 4/1996 | Jiang et al. |
| 5,514,379 A | 5/1996 | Weissleder et al. |
| 5,527,864 A | 6/1996 | Suggs et al. |
| 5,580,923 A | 12/1996 | Yeung et al. |
| 5,626,863 A | 5/1997 | Hubbell et al. |
| 5,643,596 A | 7/1997 | Pruss et al. |
| 5,645,849 A | 7/1997 | Pruss et al. |
| 5,716,408 A | 2/1998 | Eldridge et al. |
| 5,752,974 A | 5/1998 | Rhee et al. |
| 6,152,943 A | 11/2000 | Sawhney |
| 6,162,241 A | 12/2000 | Coury et al. |
| 6,165,201 A | 12/2000 | Sawhney et al. |
| 6,179,862 B1 | 1/2001 | Sawhney |
| 6,500,777 B1 | 12/2002 | Wiseman et al. |
| 6,514,534 B1 | 2/2003 | Sawhney |
| 6,566,406 B1 | 5/2003 | Pathak et al. |
| 6,605,294 B2 | 8/2003 | Sawhney |
| 6,673,093 B1 | 1/2004 | Sawhney |
| 6,703,047 B2 | 3/2004 | Sawhney et al. |
| 6,800,753 B2 | 10/2004 | Kumar |
| 6,818,018 B1 | 11/2004 | Sawhney |
| 6,833,408 B2 | 12/2004 | Sehl et al. |
| 6,936,005 B2 | 8/2005 | Poff et al. |
| 6,946,003 B1 | 9/2005 | Wolowacz et al. |

(Continued)

FOREIGN PATENT DOCUMENTS

| | | |
|---|---|---|
| EP | 2 143 737 A1 | 1/2010 |
| EP | 2177239 A2 | 4/2010 |

(Continued)

OTHER PUBLICATIONS

DynaMesh Tailored Solutions for Visceral Surgery (https://dahlhausen.de/tradepro/cms/site/PDF/dynamesh-hernia_en.pdf) (pp. 14-15) (Year: 2011).*
Extended European Search Report from Application No. EP 11187581.1 dated Aug. 1, 2014.
Canadian Office Action dated Sep. 16, 2015 in correponding Canadian Patent Application No. 2,682,464.
Japanese Office Action from Appl. No. 2011-241476 dated Oct. 1, 2015.
International Search Report from application EP 10251719.0 dated May 24, 2013.
International Search Report issued in Application EP 11250562.3 dated Dec. 8, 2011.

(Continued)

*Primary Examiner* — Tuan V Nguyen
(74) *Attorney, Agent, or Firm* — Carter, DeLuca & Farrell LLP

(57) ABSTRACT

The present disclosure relates to a medical device and methods of using the same. In embodiments, the medical device may be a buttress formed of nucleophilic buttress components and electrophilic buttress components which react to both form the buttress and provide the buttress with self-sealing capabilities after a staple or some other fixation device is placed therethrough, thereby enhancing its hemostatic properties. In other embodiments, the medical device is a hernia patch formed of a fibrous substrate, nucleophilic precursor components and electrophilic precursor components.

13 Claims, No Drawings

(56) References Cited

U.S. PATENT DOCUMENTS

| | | |
|---|---|---|
| 6,969,400 B2 | 11/2005 | Rhee et al. |
| 7,009,034 B2 | 3/2006 | Pathak et al. |
| 7,052,713 B2 | 5/2006 | Stimmeder |
| 7,176,256 B2 | 2/2007 | Rhee et al. |
| 7,347,850 B2 | 3/2008 | Sawhney |
| 8,642,085 B2 * | 2/2014 | Cassingham ........... A61P 41/00 424/486 |
| 2002/0106409 A1 | 8/2002 | Sawhney et al. |
| 2003/0031697 A1 | 2/2003 | Chudzik et al. |
| 2003/0035786 A1 | 2/2003 | Hendriks et al. |
| 2003/0073663 A1 | 4/2003 | Wiseman et al. |
| 2003/0108511 A1 | 6/2003 | Sawhney |
| 2004/0001879 A1 | 1/2004 | Guo et al. |
| 2004/0023842 A1 | 2/2004 | Pathak et al. |
| 2004/0101546 A1 | 5/2004 | Gorman et al. |
| 2004/0191277 A1 | 9/2004 | Sawhney et al. |
| 2004/0224843 A1 * | 11/2004 | Hammen ............... B01J 20/286 502/402 |
| 2004/0265371 A1 | 12/2004 | Looney et al. |
| 2005/0043814 A1 | 2/2005 | Kusanagi et al. |
| 2006/0034930 A1 | 2/2006 | Khosravi et al. |
| 2006/0099238 A1 | 5/2006 | Khosravi et al. |
| 2006/0159733 A1 | 7/2006 | Pendharkar et al. |
| 2006/0233869 A1 | 10/2006 | Looney et al. |
| 2006/0264698 A1 * | 11/2006 | Kondonis ............. A61F 2/0045 600/37 |
| 2007/0014862 A1 | 1/2007 | Pameijer et al. |
| 2007/0123817 A1 | 5/2007 | Khosravi et al. |
| 2007/0190110 A1 | 8/2007 | Pameijer et al. |
| 2007/0275073 A1 | 11/2007 | Huey et al. |
| 2008/0027365 A1 | 1/2008 | Huey |
| 2008/0114092 A1 | 5/2008 | Sawhney |
| 2008/0160051 A1 | 7/2008 | Sirota |
| 2008/0194805 A1 | 8/2008 | Vignon et al. |
| 2008/0254091 A1 * | 10/2008 | Lee ........................ D01D 5/003 424/423 |
| 2011/0070288 A1 | 3/2011 | Andjelic |
| 2011/0081397 A1 * | 4/2011 | Skalla ................... A61F 2/0063 424/423 |
| 2011/0081398 A1 * | 4/2011 | Sargeant ............. A61L 24/0031 424/423 |
| 2011/0087274 A1 | 4/2011 | Sargeant |
| 2011/0251699 A1 | 10/2011 | Ladet |
| 2013/0102959 A1 * | 4/2013 | Stopek .................. A61L 31/044 604/93.01 |
| 2013/0209659 A1 * | 8/2013 | Racenet ................ A61L 31/145 427/2.1 |
| 2014/0024639 A1 * | 1/2014 | Adams ................. C07D 211/86 514/212.03 |
| 2014/0364878 A1 * | 12/2014 | Ladet .................... A61F 2/0063 606/151 |

FOREIGN PATENT DOCUMENTS

| | | |
|---|---|---|
| EP | 2179753 A2 | 4/2010 |
| EP | 2 196 193 A1 | 6/2010 |
| EP | 2 233 160 A2 | 9/2010 |
| EP | 2 233 161 A2 | 9/2010 |
| EP | 2314254 A2 | 4/2011 |
| JP | 2008-521502 A | 6/2008 |
| JP | 2010-94519 A | 4/2010 |
| WO | 9317669 A1 | 9/1993 |
| WO | 9403155 A1 | 2/1994 |
| WO | 2010043980 A2 | 4/2010 |

OTHER PUBLICATIONS

International Search Report issued in Application EP 11250564.9 dated Dec. 8, 2011.
International Search Report issued in Application EP 11250563.1 dated Dec. 27, 2011.
International Search Report issued in Application EP 11250566.4 dated Dec. 22, 2011.
International Search Report issued in Application EP 11250565.6 dated Dec. 23, 2011.
European Search Report for EP 09252417.2-1219 date of completion is Dec. 6, 2010 (3 pages).
European Search Report for EP 09252421.4-1219 date of completion is Dec. 6, 2010 (3 pages).
Extended European Search Report from EP Appl. No. 16157565.9 dated Jun. 24, 2016.
European examination report issued in Appl. No. 16 157 565.9 dated Mar. 23, 2018 (5 pages).
Australian Examination Report No. 1 issued in corresponding Appl. No. 2016201227 dated Sep. 25, 2019 (4 pages).
Kasahara, et al., "Polyglycolic acid sheet with fibrin glue potentiates the effect of a fibrin-based haemostat in cardiac surgery", Journal of Cardiothoracic Surgery, 9:121. pp. 1-4 (2014).
Notice of Opposition issued in corresponding European Patent No. 3061471 dated Apr. 30, 2020, (30 pages).

* cited by examiner

MEDICAL DEVICES WITH SEALING PROPERTIES

CROSS-REFERENCE TO RELATED APPLICATIONS

The present application claims priority to, and the benefit of, U.S. Provisional Patent Application Ser. No. 62/121,831, filed on Feb. 27, 2015, the entire contents of which are hereby incorporated by reference.

BACKGROUND

The present disclosure relates to medical devices, including surgical devices such as buttresses for use with wound closure devices, hernia patches, tissue scaffolds, and the like, which can be used with tissue fixation devices. Medical devices formed of the materials of the present disclosure are capable of enhancing tissue repair, promoting hemostasis, and the like.

Surgical stapling instruments are employed by surgeons to sequentially or simultaneously apply one or more rows of fasteners, e.g., staples or two-part fasteners, to body tissue for the purpose of joining segments of body tissue together. Such devices generally include a pair of jaws or finger-like structures between which the body tissue to be joined is placed. When the stapling device is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the device to cut the tissue between the lines of staples.

When stapling certain tissue, such as lung, esophageal, intestinal, duodenal, and vascular tissues, or relatively thin or fragile tissues, it may be desirable to seal the staple line against air or fluid leakage. Preventing or reducing air or fluid leakage can significantly decrease post-operative recovery time. Additionally, it may be desirable to reinforce the staple line against the tissue to prevent tears in the tissue or pulling of the staples through the tissue. One method of preventing tears or pull throughs involves the placement of a biocompatible fabric reinforcing material, sometimes referred to herein, in embodiments, as a "buttress" material, between the staple and the underlying tissue.

For hernia repair, fasteners have been used to attach a mesh or patch over the hernia defect so that bowel and other abdominal tissue are blocked from forming an external bulge that is typical of abdominal hernias. Adequate tissue ingrowth of the patch is important for both sealing and preventing tears in the patch used to repair the hernia.

Improved surgical repair materials, capable of use as buttresses for sealing and/or reinforcing staple lines against tissue, and/or use as a hernia patch for sealing and reinforcing a hernia repair, remain desirable.

SUMMARY

The present disclosure relates to surgical repair devices, including surgical buttresses and/or hernia patches, which can be used with tissue fixation devices, and methods of using the same.

Medical devices of the present disclosure include surgical buttresses, hernia patches, tissue scaffolds and the like. The thickness of the medical device will depend, in part, upon its intended use, and may be from about 0.1 mm to about 3 mm.

In embodiments, a buttress of the present disclosure includes a body including the reaction product of a nucleophilic buttress component and an electrophilic buttress component; and a fibrous substrate, wherein the buttress has a thickness from about 0.1 mm to about 0.5 mm.

In embodiments, the reaction product of the nucleophilic buttress component and the electrophilic buttress component is a foam.

In embodiments, the buttress has a film on a surface thereof.

Methods of the present disclosure include, in embodiments, contacting a fibrous substrate with a nucleophilic precursor component in solution to form a medical device precursor; lyophilizing the medical device precursor; contacting an electrophilic precursor component with the medical device precursor; and allowing the nucleophilic precursor component and the electrophilic precursor component to react to form a medical device.

In other embodiments, methods of the present disclosure include, contacting a nucleophilic medical device component in solution with an electrophilic medical device component; allowing the nucleophilic medical device component to react with the electrophilic medical device component to form a medical device precursor; and lyophilizing the medical device precursor to form a foam.

In other embodiments, methods of the present disclosure include lyophilizing a nucleophilic medical device precursor component to form a foam; applying a layer of an electrophilic medical device precursor component to the foam, and allowing the nucleophilic medical device precursor component and electrophilic medical device precursor component to react to form a medical device.

In embodiments of the present disclosure, a hernia patch includes a body including the reaction product of a nucleophilic precursor component and an electrophilic precursor component; and a fibrous mesh substrate, wherein the hernia patch has a thickness from about 0.3 mm to about 2.5 mm.

DETAILED DESCRIPTION

Various exemplary embodiments of the present disclosure are discussed herein below in terms of buttresses for use with tissue fixation devices, in embodiments surgical staples. While the below disclosure discusses in detail the use of these buttresses with staples, it will be appreciated that buttresses of the present disclosure may be used with any fixation device utilized to close any wound, defect, and/or opening in tissue. Thus, while the surgical buttresses are discussed in conjunction with a surgical stapling apparatus, it is envisioned that the principles of the present disclosure are equally applicable to a range of buttressing materials and film-based medical devices that are used to mechanically support tissues, reinforce tissues along staple or suture lines, and decrease the incidence of fluid leakage and/or bleeding of tissue.

Other exemplary embodiments of the present disclosure are discussed hereinbelow in terms of hernia patches or hernia meshes (said terms being used interchangeably).

In embodiments, buttresses described herein may be used in sealing a wound by approximating the edges of wound tissue between a staple cartridge and an anvil of a stapling apparatus which contains at least one buttress. Firing of the stapling apparatus forces the legs of at least one staple to pass through the opening on the staple cartridge, the at least one buttress, tissue, and the openings on the anvil to seal the tissue. The compressive force of the anvil against the staple cartridge and/or the openings created by the passage of the staple legs through the buttress may affix the buttress thereto in order to advantageously reducing bleeding, assisting in sealing the wound, and allowing tissue ingrowth, if desired. Thus, the present disclosure describes surgical buttresses, and methods and mechanisms for using the same, for the targeted delivery of active or passive hemostatic agents to a specific surgical site.

In embodiments, a buttress of the present disclosure may be coated and/or formed of materials, referred to in embodiments as components, which will form a buttress. These components, when used to form a buttress or any portion thereof, may further promote hemostasis and/or assist in sealing any holes formed in the buttress as a result of staples or other fixation device(s) being fired/applied therethrough.

In other embodiments, materials of the present disclosure, formed of components similar to those used to form buttresses as described above, may be used to form medical devices such as hernia patches, tissue scaffolds, staple buttresses, and the like.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

Medical devices of the present disclosure, including surgical buttresses, hernia patches, tissue scaffolds, and the like, may be fabricated from a biocompatible material which is a bioabsorbable or non-absorbable, natural or synthetic material. It should of course be understood that any combination of natural, synthetic, bioabsorbable, and/or non-bioabsorbable materials may be used to form a medical device of the present disclosure.

The medical device may also be formed of materials that are porous, non-porous, or combinations thereof.

In embodiments, a medical device of the present disclosure may be formed of precursor components capable of enhancing the sealing properties of any medical device possessing same. These materials may, in embodiments, result in a medical device that possesses self-sealing properties, i.e., the ability of a surgical buttress and/or hernia patch to seal itself after a staple or other tissue fixation device has been deployed therethrough, forming a hole(s) within any portion of the buttress and/or patch.

In embodiments, a medical device of the present disclosure may be fashioned of a first precursor component that is nucleophilic, or that has been functionalized to possess nucleophilic groups thereon. Suitable nucleophilic components include, for example, functional polymers such as proteins, poly(allyl amine), styrene sulfonic acid, and/or amine-terminated di- or multifunctional poly(ethylene glycol) ("PEG").

In embodiments, collagen may be used to form a medical device of the present disclosure. As collagen possesses primary amines from lysine groups, the collagen is a nucleophilic material. Other nucleophilic groups that may be present on the first component include thiols, and the like.

In embodiments, collagen of human and/or animal origin, e.g., type I porcine or bovine collagen, type I human collagen, or type III human collagen, may be used to form a medical device such as a surgical buttress, a hernia patch, and/or layer(s) thereof. In embodiments, the collagen may be oxidized or a mixture in any proportion of non-oxidized and oxidized collagens. In embodiments, oxidized or non-oxidized collagen may be lyophilized, freeze-dried, or emulsified in the presence of a volume of air to create a foam and then freeze-dried, to form a porous compress.

In embodiments, a medical device of the present disclosure may be made from denatured collagen or collagen which has at least partially lost its helical structure through heating or any other method. The term "denatured collagen" means collagen which has lost its helical structure. The collagen as described herein may be native collagen or atelocollagen. The collagen may have been previously chemically modified by oxidation, methylation, succinylation, ethylation, or any other process within the purview of one skilled in the art.

In embodiments, collagen may be combined with a second nucleophilic material as the first component. For example, collagen may be combined with trilysine, and this combination of nucleophilic materials may be used as a first precursor component of a medical device of the present disclosure.

Medical devices of the present disclosure may also include a second precursor component which is electrophilic, capable of reacting with the nucleophilic materials used to form the medical device.

Thus, for example, if the first precursor component used to form a medical device of the present disclosure has nucleophilic functional groups such as amines, the second precursor component used to form a medical device of the present disclosure may have electrophilic functional groups thereon. Suitable electrophilic groups are within the purview of those skilled in the art and include, but are not limited to, N-hydroxysuccinimides, sulfosuccinimides, combinations thereof, and the like.

Each of the first and second precursor components used to form a medical device of the present disclosure is multifunctional, meaning that it includes two or more nucleophilic or electrophilic functional groups, such that, for example, a nucleophilic functional group on the first precursor component may react with an electrophilic functional group on the second precursor component to form a covalent bond. At least one of the first or second precursor components includes more than two functional groups, so that, as a result of nucleophilic-electrophilic reactions, the precursor components combine to form cross-linked polymeric products.

In embodiments, a multifunctional nucleophilic polymer such as collagen or trilysine, or combinations thereof, may be used as a first nucleophilic precursor component, and a multifunctional electrophilic polymer such as a multi-arm PEG functionalized with multiple NHS groups may be used as a second electrophilic precursor component. The multi-arm PEG functionalized with multiple NHS groups can, for example, have four, six or eight arms and a molecular weight of from about 2,000 to about 25,000. Other examples of suitable first and second components are hydrogel precursors as described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated by reference herein.

The precursor components used to form a medical device of the present disclosure may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose and/or hydroxymethylcellulose; hyaluronic acid; and proteins such as albumin, collagen, casein, and gelatin. In embodiments, combinations of the foregoing polymeric materials may be utilized to form a core. The polyethers, and more particularly poly(oxyalkylenes) or poly(ethylene glycol) or polyethylene glycol ("PEG"), may be utilized in some embodiments.

When the core is small in molecular nature, any of a variety of hydrophilic functionalities may be used to make the nucleophilic and/or electrophilic precursor components water soluble. In embodiments, functional groups like hydroxyl, amine, sulfonate and carboxylate, which are water soluble, may be used to make a nucleophilic and/or electrophilic precursor component water soluble. For example, the N-hydroxysuccinimide ("NHS") ester of subaric acid is insoluble in water, but by adding a sulfonate group to the succinimide ring, the NHS ester of subaric acid may be made water soluble, without affecting its ability to be used as a reactive group due to its reactivity towards amine groups.

In some cases, additional nucleophilic components and/or electrophilic components may be added to the precursor components used to form a medical device of the present disclosure. These additional materials/components may assist in stabilizing the precursor components used to form a buttress and/or hernia patch formed in accordance with the present disclosure and help absorb any excess nucleophilic components and/or electrophilic components used to form the medical device.

The reaction conditions for forming medical devices from the nucleophilic and electrophilic precursor components described above may depend on the nature of the reactive component used. In embodiments, reactions are conducted in buffered aqueous solutions at a pH of about 5 to about 12. Buffers include, for example, sodium borate buffer (pH 10) and triethanol amine buffer (pH 7). In some embodiments, organic solvents such as ethanol or isopropanol may be added to improve the reaction speed or to adjust the viscosity of a given formulation.

When the nucleophilic and/or electrophilic precursor components used to form a medical device of the present disclosure are synthetic (for example, when they are based on polyalkylene oxide), it may be desirable to use molar equivalent quantities of the reactants.

When choosing the nucleophilic and electrophilic precursor components, at least one of the precursor components may have more than two functional groups per molecule and, if it is desired that the resultant medical device be biodegradable, at least one degradable region. In embodiments, each nucleophilic precursor component and electrophilic precursor component may have more than two functional groups, and in embodiments, more than four functional groups.

The crosslinking density of the resultant medical device may be controlled by the overall molecular weight of the nucleophilic and electrophilic precursor components, and the number of functional groups available per molecule. A lower molecular weight between crosslinks, such as 600 Da, will give much higher crosslinking density as compared to a higher molecular weight, such as 10,000 Da. Elastic materials may be obtained with higher molecular weight functional polymers with molecular weights of more than 3000 Da.

The crosslinking density may also be controlled by the overall percent solids of the nucleophilic and electrophilic components in solution(s). Increasing the percent solids increases the number of crosslinkable groups per unit volume and potential crosslinking density. Yet another method to control crosslink density is by adjusting the stoichiometry of nucleophilic groups to electrophilic groups. A one to one ratio may lead to the highest crosslink density, however, other ratios of reactive functional groups (e.g. nucleophile: electrophile) are envisioned to suit a desired formulation.

The medical devices of the present disclosure, such as a surgical buttress, hernia patch, tissue scaffold, and the like, may also be biodegradable, so that the device does not have to be retrieved from the body. The term "biodegradable" as used herein is defined to include both bioabsorbable and bioresorbable materials. By biodegradable, it is meant that the medical device decomposes, or loses structural integrity under body conditions (e.g., enzymatic degradation or hydrolysis), or is broken down (physically or chemically) under physiologic conditions in the body such that the degradation products are excretable or absorbable by the body.

Degradable medical devices degrade due to hydrolysis of any biodegradable region. The degradation of medical devices containing synthetic peptide sequences may depend on the specific enzyme necessary for degradation of the sequence and its concentration. In some cases, a specific enzyme may be added during the crosslinking reaction to accelerate the degradation process.

The first and second precursor components may be combined using any suitable method within the purview of those skilled in the art. For example, the first nucleophilic precursor component used to form the medical device of the present disclosure may be soluble and dissolved in a suitable solvent to form a solution. Any solutions, including one or both of the nucleophilic and/or electrophilic precursor components used to form a medical device, should not contain harmful or toxic solvents.

Suitable solvents include, for example, deionized water, and the like. In some cases, it may be desirable to adjust the pH of the nucleophilic precursor component in solution through the addition of suitable biocompatible acids, bases, buffers, combinations thereof, and the like. Suitable acids include, for example, hydrochloric acid, and the like, to reach a pH from about 2.5 to about 3.5, in embodiments about 2.8. Suitable bases include, for example, sodium hydroxide, and the like, in a solution at a concentration from about 1.5% by weight to about 2.5% by weight, in embodiments from about 1.7% by weight to about 2.2% by weight, to reach a pH from about 6.5 to about 7.5, in embodiments from about 6.7 to about 7.2. Suitable buffers include, for example, 4-Morpholinepropanesulfonic acid (MOPS), sodium phosphate dibasic, sodium phosphate monobasic, combinations thereof, and the like, at a concentration from about 5 mmol to about 15 mmol, in embodiments from about 7 mmol to about 12 mmol.

As noted above, in embodiments the nucleophilic precursor component used to form a medical device of the present disclosure may include collagen. In embodiments, the nucleophilic precursor component may include both collagen and trilysine. For example, in embodiments, purified porcine collagen (CPP) may be dissolved in deionized water and the pH adjusted to from about 7 to about 7.3 by the addition of 1 N (normal) sodium hydroxide and MOPS.

The amount of time for gelation to occur, i.e., the time for the nucleophilic precursor component to react with the electrophilic precursor component, will be influenced by the pH of the CPP solution. A more acidic pH will result in a longer gelation time, while a more basic pH will result in a shorter gelation time.

In embodiments, it may be desirable to add a polyol and/or an alcohol to the composition to aid in the formation of a thinner, softer medical device of the present disclosure, in embodiments a surgical buttress. Suitable alcohols which may be added after, or in combination with, a suitable buffer as described above include, for example, glycerol. A polyethylene glycol dimethyl ether might also be used. Where utilized, this alcohol may be added in an amount from about 0.025% to about 0.5% by weight of solution including the first component used to form the medical device, in embodiments from about 0.1% to about 0.3% by weight of solution including the first precursor component used to form the medical device.

Where a combination of nucleophilic materials is used as the nucleophilic precursor component, for example collagen and trilysine, the collagen may be present in an amount from about 0.8% by weight to about 1.4% by weight of the nucleophilic precursor component, in embodiments from about 0.9% by weight to about 1.3% by weight of the nucleophilic precursor component, with the trilysine present in an amount from about 0.05% by weight to about 0.25% by weight of the nucleophilic precursor component, in embodiments from about 0.1% by weight to about 0.2% by weight of the nucleophilic precursor component.

The electrophilic precursor component used to form a medical device of the present disclosure may then be added to this solution. For example, in embodiments, a multi-armed polyethylene glycol having a molecular weight of about 2000 Daltons, functionalized with succinimidyl glutarate groups, which may have 4 arms and be referred to herein as a 4 arm 2 k PEG SG, may then be blended with the collagen solution described above once a pH of about 7.0 is obtained. The NHS ester reacts with the primary amine from the lysine groups on the CPP, thereby forming a stable amide bond. This bond may result in a tailored degradation time of the resulting device, such as a buttress or hernia patch. The ester group in the newly formed gel will also break down over time, permitting the medical device to degrade in vivo over a period from about 3 weeks to about 12 weeks, in embodiments from about 4 weeks to about 7 weeks.

As noted above, in embodiments the electrophilic precursor component may also be in solution, in embodiments using any solvent described as suitable for forming a solution with the nucleophilic precursor component, and the two solutions may be combined.

Methods for combining the nucleophilic and electrophilic precursor components are within the purview of those skilled in the art. For example, the blending of the two precursor components may be simply by placing the nucleophilic precursor component solution in a first syringe of a dual syringe device, the electrophilic precursor component in a solution in the second syringe, and then permitting the two solutions to mix via a luer assembly as a plunger is pressed to expel the contents of the two syringes from the device thereby forming a blended solution. Dual syringes and/or similar devices suitable for use in applying more than one solution, include, for example, those described in U.S. Pat. Nos. 4,874,368; 4,631,055; 4,735,616; 4,359,049; 4,978,336; 5,116,315; 4,902,281; 4,932,942; 6,179,862; 6,673,093; 6,152,943; and 7,347,850.

The blended solution may be poured into a dish and the nucleophilic and electrophilic precursor components allowed to react to form an intermediate medical device precursor material. The intermediate medical device precursor is then lyophilized, resulting in a thin foam. Methods for lyophilization are within the purview of those skilled in the art and include the use of vacuum ovens.

The medical device formed of materials of the present disclosure may include the first nucleophilic precursor component in an amount from about 10% to about 30% by weight of the medical device, in embodiments from about 15% to about 25% by weight of the medical device, and the second electrophilic precursor component in an amount from about 70% to about 90% by weight of the medical device, in embodiments from about 75% to about 85% by weight of the medical device. In other embodiments, the medical device may include the first nucleophilic precursor component in an amount from about 70% to about 90% by weight of the medical device, in embodiments from about 75% to about 85% by weight of the medical device, and the second electrophilic precursor component in an amount from about 10% to about 30% by weight of the medical device, in embodiments from about 15% to about 25% by weight of the medical device.

Optionally, in some embodiments, an additional nucleophile, such as trilysine, optionally in solution, may then be added after lyophilization in order for the stabilized cross linked collagen to absorb the trilysine. The materials may then be subjected to an optional second lyophilization cycle, resulting in a dry foam product.

After the optional second lyophilization, an optional additional electrophilic material may be added to the dry product. For example, a film formed of a multi-armed polyethylene glycol having a molecular weight of about 15000 Daltons, functionalized with succinimidyl succinate groups, which may have 8 arms and be referred to herein as an 8 arm 15 k PEG SS, may be applied as a film to the dry foam product described above.

Medical devices of the present disclosure, including surgical buttresses, hernia patches, tissue scaffolds, and the like, may be used by themselves or may be combined with additional materials to form a desired medical device. For example, the dry foam product produced in accordance with the present disclosure is very soft and flexible when hydrated. This softness may be advantageous for repositioning the medical device, in embodiments a surgical buttress or hernia patch, prior to firing a staple and/or applying any other fixation device to which the medical device will become attached.

However, where additional strength may be desired, a nonwoven buttress material or mesh material may be incorporated into the dry foam product prior to cross-linking. For example, a nonwoven buttress or mesh material may be placed in a dish prior to addition of the first nucleophilic precursor component and/or the second electrophilic precursor component. The nucleophilic solution/gel, for example a collagen, hydrates the nonwoven fabric, and becomes a single surgical buttress or hernia patch after cross-linking with the electrophilic component, such as a functional PEG, and subsequent lyophilization.

In embodiments, rather than combining the electrophilic precursor component with the nucleophilic precursor component in solution, the nucleophilic precursor component in solution may be added to a substrate to form a medical device precursor, which is then lyophilized. After lyophilization, the medical device precursor may be coated with the electrophilic precursor component in a solution to form a film thereon. The nucleophilic precursor component of the medical device precursor and the electrophilic precursor component then react to form a medical device, such as a buttress, hernia patch, tissue scaffold, and the like.

Medical devices of the present disclosure, such as surgical buttresses, with or without a fibrous material as a part thereof, may have a thickness from about 0.1 mm to about 0.5 mm, in embodiments from about 0.2 mm to about 0.4 mm.

Other non-limiting examples of materials which may be used in forming a medical device of the present disclosure, for example additional layers of a surgical buttress or hernia patch to which the above CPP foam may be applied, include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and combinations thereof.

In embodiments, natural biological polymers may be used in forming a portion of a medical device of the present disclosure. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitin, chitosan, and combinations thereof. In addition, natural biological polymers may be combined with any of the other polymeric materials described herein to produce a medical device of the present disclosure.

A medical device of the present disclosure, such as a surgical buttress, hernia patch, tissue scaffold, and the like, may also possess additional porous material(s). Any porous portion of a medical device of the present disclosure may have openings or pores over at least a part of a surface thereof. Suitable porous materials for forming additional layers and/or portions of a medical device of the present disclosure include, but are not limited to, fibrous structures (e.g., knitted structures, woven structures, non-woven structures, etc.) and/or foams (e.g., open or closed cell foams). In embodiments, the pores may be in sufficient number and size so as to interconnect across the entire thickness of the medical device. Woven fabrics, knitted fabrics and open cell foam are illustrative examples of structures in which the pores can be in sufficient number and size so as to interconnect across the entire thickness of the medical device. In embodiments, the pores may not interconnect across the entire thickness of the medical device. Closed cell foam or fused non-woven materials are illustrative examples of structures in which the pores may not interconnect across the entire thickness of the medical device. In other embodiments, the pores of the medical device may span across the entire thickness of medical device. In yet other embodiments, the pores do not extend across the entire thickness of the medical device. In some embodiments, pores may be located on a portion of the medical device, with other portions of the medical device having a non-porous texture. Those skilled in the art may envision a variety of pore distribution patterns and configurations for the porous medical device.

Fibrous supports of the present disclosure, especially those used to form hernia patches, may have sizes (width× height) from about 1.4 mm×0.4 mm to about 2.8 mm×3.0 mm, in embodiments from about 1.7 mm×1.4 mm to about 2.2 mm×2.4 mm. The % effective porosity (pores >1 mm) may be from about 3% to about 72%, in embodiments from about 10% to about 57%.

Where a porous portion of the medical device is fibrous, the fibers may be filaments or threads suitable for knitting or weaving or may be staple fibers, such as those frequently used for preparing non-woven materials. Suitable techniques for making fibrous structures are within the purview of those skilled in the art.

Some non-limiting examples of materials from which the fibers may be made include, but are not limited to, polyesters such as poly(lactic acid) and poly(glycolic acid) poly(trimethylene carbonate), poly(dioxanone), poly(hydroxybutyrate), poly(phosphazine), polyethylene terephthalate, ultra-high molecular weight polyethylene, polyethylene glycols, polyethylene oxides, polyacrylamides, polyhydroxyethylmethylacrylate (pHEMA), polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, poly (saccharides), polyamides, poly(iminocarbonates), polyalkylene oxalates, polyoxaesters, polyorthoesters, polyphosphazenes, biopolymers, polymer drugs and copolymers, block copolymers, homopolymers, blends and combinations thereof.

Where the medical device includes fibrous materials, the medical device may be formed using any suitable method including, but not limited to, knitting, weaving, non-woven techniques (including melt blown), wet-spinning, electrospinning, extrusion, co-extrusion, and the like. Suitable techniques for making fibrous structures are within the purview of those skilled in the art. In embodiments, the medical device may be a surgical buttress possessing a three dimensional structure, such as the textiles described in U.S. Pat. Nos. 7,021,086 and 6,443,964, the entire disclosures of each of which are incorporated by reference herein.

In some embodiments, the medical device of the present disclosure includes fibers of oxidized cellulose. Such materials are known and include oxidized cellulose hemostat materials commercially available under the trade name SURGICEL®. Methods for preparing oxidized cellulose hemostat materials are within the purview of those skilled in the art and are disclosed, for example, in U.S. Pat. Nos. 3,364,200, 4,626,253, 5,484,913, and 6,500,777, the entire disclosures of each of which are incorporated by reference herein.

In other embodiments, the medical devices of the present disclosure may include fibers of poly(glycolic acid). Such materials include, for example, those commercially available from Covidien under the trade name DEXON®.

Foams utilized in the construction of a medical device of the present disclosure may enhance the ability of the medical device to absorb fluid, reduce bleeding, and seal any wound or tissue defect, in embodiments a surgical wound or hernia. Also, a porous foam may allow for tissue ingrowth to fix the medical device in place.

As noted above, the medical device of the present disclosure may be used with any fixation device to further assist in sealing tissue. For example, medical devices of the present disclosure may be used in conjunction with staples, tacks, clips, sutures, combinations thereof, and the like.

In embodiments, medical devices of the present disclosure may be used with staples. For example, a surgical buttress formed of a medical device of the present disclosure is provided to reinforce and seal the lines of staples applied to tissue by a surgical stapling apparatus. The buttress may be configured into any shape, size, or dimension suitable to fit any surgical stapling, fastening, or firing apparatus.

In embodiments, the buttresses described herein may be used in sealing a wound by approximating the edges of wound tissue between a staple cartridge and an anvil of a surgical stapling apparatus which contains the buttress. Firing of the surgical stapling apparatus forces the legs of at least one staple to pass through the opening on the staple cartridge and the buttress, the tissue, and the openings on the anvil to secure the buttress to the tissue, to secure the adjoining tissue to one another, and to seal the tissue.

Where the medical device of the present disclosure is used to form a surgical buttress, upon application to a site of bleeding tissue, the buttress may affect hemostasis of said tissue. As used herein, the term "hemostasis" means the arrest of bleeding. It is believed, without being limited to any theory, that the hemostatic effect of the buttress is due to both intrinsic and extrinsic factors. In embodiments, the buttress may include a hemostatic agent providing an intrinsic hemostatic effect. In other embodiments, the cross-linking between the nucleophilic and electrophilic components used to form the buttress creates a physical barrier to blood flow, thereby providing an extrinsic hemostatic effect.

Hemostasis may occur, at the site of application of the buttress, within less than about 2 minutes. As stated above, upon contact with tissue, such as, for example, injured or bleeding tissue, in embodiments the buttress soaks up interstitial and physiological fluid (e.g., blood, lymph-fluid, etc.) and the nucleophilic and electrophilic components may mix and further react to enhance the sealing of any holes formed in the buttress as well as the tissue being joined by the fixation device(s).

Where a medical device of the present disclosure is used as a hernia patch, similar to the surgical buttress described above, the hernia patch may be affixed to tissue using fixation device(s), including a suture, a screw, a tack, an adhesive, a sealant, combinations thereof, and the like. For hernia repair, the device should be strong enough to provide tissue support and, in some cases, should also permit tissue integration after implantation.

In use, a hernia patch formed of a medical device of the present disclosure is provided to reinforce and close a hernia. The hernia patch may be configured into any shape, size, or dimension suitable to close the hernia to be fixed. Hernia patches of the present disclosure have a fibrous material as described above as a part thereof. The hernia patch may have a thickness from about 0.3 mm to about 2.5 mm, in embodiments from about 0.5 mm to about 1 mm.

In embodiments, it may be desirable to provide a variety of hernia patches having different sizes so that a surgeon can select a patch of suitable size to treat a particular patient. This allows patches to be completely formed before delivery, ensuring that the smooth edge of the patch is properly formed under the control of the manufacturer. The surgeon would thus have a variety of differently sized (and/or shaped) patches to select the appropriate implant to use after assessment of the patient. In other embodiments, the patch can be cut to any desired size. The cutting may be carried out by a surgeon or nurse under sterile conditions such that the surgeon need not have many differently sized patches on hand, but can simply cut a patch to the desired size after assessment of the patient. In other words, the patch may be supplied in a large size and be capable of being cut to a smaller size, as desired.

Additionally, the medical device of the present disclosure may include biologically acceptable additives such as plasticizers, antioxidants, dyes, dilutants, therapeutic agents, and the like and combinations thereof, which can be coated on the buttress, or impregnated into the buttress (e.g., during formation). Suitable dyes include, but are not limited to, carbon black, bone black, D&C Green No. 6, and D&C Violet No. 2. A dye such as D&C Green No. 6 may be added to the filaments used to form the fibers in a suitable amount, in embodiments from about 0.05% by weight to about 1% by weight, in embodiments about 0.1% by weight.

Therapeutic agents include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MC SF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In embodiments, the therapeutic agent may include at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine); agents useful for calcium regulation (e.g., calcitonin, and parathyroid hormone); antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, and epinephrine); anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds and hormones (e.g., androgens such as danazol, testosterone cypionate, fluoxymesterone, ethyltestosterone, testosterone enathate, methyltestosterone); estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutarnide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepam, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the therapeutic agent may be water soluble. In some embodiments, the therapeutic agent may not be water soluble.

In embodiments, the above therapeutic agents may be applied to a medical device of the present disclosure in a solution. Where the therapeutic agent is water soluble, water may be used as a solvent for forming such a solution. Other solvents which may be used include polar and non-polar solvents including, but not limited to, alcoholsmethanol, ethanol, propanol chlorinated hydrocarbons such as methylene chloride, chloroform, 1,2-dichloro-ethane aliphatic hydrocarbons such as hexane, heptene, ethyl acetate, combinations of the foregoing, and the like.

Several embodiments of the disclosure are described below with reference to the following non-limiting Examples. The Examples are intended to be illustrative only and are not intended to limit the scope of the present disclosure. As used herein, "room temperature" refers to a temperature of from about 20° C. to about 30° C. Also, parts and percentages, such as solution percentages, are by weight unless otherwise indicated.

Example 1

A foam was produced as follows. About 0.5713 grams of purified porcine collagen (CPP) (at 13.5% moisture, actual weight estimate was 0.4970 grams) was dissolved in about 43.184 grams 18 mΩ deionized water. The collagen and water were mixed in a water bath at about 700 revolutions per minute (rpm) at about 36° C. After about 90 minutes, the CPP was completely in solution, so about 110 mg of trilysine was added thereto. Also, about 2.56 grams of water was added to account for evaporation of about 1.67 grams. The tare weight after about 10-15 minutes was about 101.61 grams, and the solution was clear again (concentration of CPP in solution was about 1.14% by weight).

The following day, the pH of the solution was adjusted with sodium hydroxide (NaOH) and 4-Morpholinepropanesulfonic acid (MOPS) as follows.

Upon examination, the solution was still clear and remained warm with a pH of 4.34. About 1N NaOH was slowly added dropwise with stirring at about 700 rpm. About 0.49 grams of NaOH was added over about 4 minutes to get to a pH of about 6.60. The resulting solution was slightly cloudy.

About 0.072 grams (about 7.8 millimolar) of MOPS was then added. The pH fell to about 6.19.

About 0.79 grams 1N (NaOH) was added and the pH rose to a target of 7.28. The concentration of CPP was about 1.11% by weight. An additional 0.30 grams of 1N NaOH solution was added (0.79 grams total) to increase the pH.

About 0.060 grams of glycerol was then added to the solution.

Three sample buttresses were then prepared using the above solution.

The first sample (sometimes referred to herein as "Sample 1") was prepared by adding about 13.75 grams of the above solution to a square dish and a nonwoven fabric (having a weight of about 0.09 grams) formed of a homopolymer of glycolic acid. Sample 1 included about 0.152 grams (about 1.10% by weight) CPP and about 33 mg (about 0.24% by weight) trilysine.

The second sample (sometimes referred to herein as "Sample 2") was prepared by adding about 14.07 grams of the combined solution to a square dish. This sample included about 33 mg of trilysine and about 0.155 grams CPP.

The third sample (sometimes referred to herein as "Sample 3") was prepared by adding the remaining solution to a 20 cc syringe and pushed through a 1.0 μm PTFE filter. About 14 grams of the combined filtered solution was added to a square dish. This sample contained about 33 mg of trilysine and about 0.155 grams CPP. There was no difference in the appearance of the solution, so it does not appear that filtering made any difference when comparing Samples 2 and 3, as the collagen squares had the same weights after lyophilization.

The solutions for all three Samples thickened in about 15 minutes. The dishes were allowed to sit under ambient conditions for close to 2 hours, after which time they were added to a lyophilizer (a vacuum oven).

The samples were removed from the vacuum oven after about 2-3 days and packaged under a nitrogen blanket. All pieces were soft, thin and flexible. The solution incorporated into the fabric sample (Sample 1) very nicely and was also perfectly flat.

Example 2

The following day, the edges of Sample 2 from Example 1 above were trimmed to form a buttress having a dimension of 72×81 mm (58 cm$^2$).

A layer of PEG film, having a weight of about 0.162 grams, was applied to the dry trimmed sheet, so that the coated sheet weighed about 0.81 grams. The amount of PEG was present in an amount of about 11.1 mg PEG/cm$^2$. The trilysine was present in an amount of about 0.36 mg trilysine/cm$^2$.

6 samples of Sample 2 were subjected to burst testing. Briefly, a TA.XT Plus Texture Analyzer (TA) was used to cycle a probe on the hydrated buttress sample at a certain force level, allowing the product to gel on a polyurethane foam plate. The test sample was placed over a small opening at the center of the plate. A response was monitored on the instrument and a pattern was generated over the course of the cycle. The plate was then placed on another device which locked the plate in place. A syringe pump then applied pressure to the base of the plate. Pressure was monitored until the test sample began to leak.

About 80 μL of phosphate buffered solution (PBS) was initially added, but more was added as it seemed to wet only one side. Only 2 samples gave actual burst values (the process was adjusted for correct volume of PBS addition). The best sample weighed only 19 mg using a 9/16 inch punch. This sample gave a nice gel curve at a pressure of 264 mm Hg, as the burst failed through the center. The other sample weighed about 17 mg, where more than 125 μL PBS was added. This sample had a burst at a pressure of 60 mm Hg with failure through the side. There were heavier samples having weights from 21-24 mg. The PEG was observed as a ring outside the sample on the heaviest samples.

Example 3

Sample 3 from Example 1 was used for this Example. The edges of Sample 3 were trimmed to form a buttress having a dimension of 75×80 mm (60 cm$^2$).

A layer of PEG film, having a weight of about 0.193 grams, was applied to the dry trimmed sheet, so that the coated sheet weighed about 0.65 grams. The amount of PEG was present in an amount of about 7.5 mg PEG/cm$^2$. The trilysine was present in an amount of about 0.36 mg trilysine/cm$^2$.

Samples of Sample 3 were subjected to burst testing as described above in Example 2, using the following parameters:
1. Sample weight of about 22.3 mg (0.34 mm thick) was hydrated with about 110 μL PBS and allowed to gel on the TA. This resulted in excellent burst formation at 141 mm Hg. The initial sample was added to PBS buffer and lasted about 5-7 days in a 37° C. bath.
2. Sample weight of about 17.9 mg (0.28 mm thick) was added to about 110 μL PBS and allowed to gel on the TA. Burst formation at about 65 mm Hg.
3. Sample weight of about 18.4 mg (0.2 mm thick on snap gauge) was hydrated with about 110 μL PBS and allowed to gel on the TA. Burst formation was observed at about 100 mm Hg.
4. Sample weight of about 20.4 mg (0.375 mm thickness) was hydrated with about 110 μL PBS and allowed to gel on the TA. Burst formation was at about 24 mm Hg.
5. Sample weight of about 17.9 mg (0.355 mm thickness was hydrated with about 110 μL PBS and allowed to gel on the TA. A curve displaying gel time was observed on the TA with burst occurring at about 450 mm Hg. Sample weight about 30.4 mg after burst.

Example 4

Sample 1 from Example 1 above was sealed under a nitrogen blanket in a foil pouch for about 10 days. The piece which had fabric formed of a homopolymer of glycolic acid incorporated in the foam measured about 61.5×51.5 mm and weighed about 0.184 grams.

The same lot of fabric with the same dimensions was obtained having a weight of 0.083 grams.

Approximately 0.6 grams of a block of an 8-armed polyethylene glycol having a molecular weight of about 15000 Daltons, functionalized with succinimidyl succinate groups (8 arm 15 k PEG SS) was melted on a piece of release paper with a hot plate. A Mylar sheet was placed over the PEG and a roller was used to make a very thin film of PEG. The sheet was moved to a dry box under nitrogen flow to cool. Later, the release paper was removed, showing a thin layer of PEG on the Mylar. This piece was then placed back on the hot plate where the PEG film melted. The 31.7 cm$^2$ piece of collagen/fabric (Sample 1) was laid on the warm PEG with the collagen side down. The roller was used again to help transfer. The Mylar/PEG/collagen/fabric unit was immediately moved to a nitrogen dry box and stored overnight.

The next day, the Mylar was removed and the PEG was observed to have adhered to the collagen. The amount of PEG film was about 9.8 mg/cm$^2$ PEG layer of film on the collagen.

Burst testing was performed on samples as described above in Example 3, but for these samples, the PBS buffer could not be directly applied to the collagen/PEG as the PEG side was facing down and partially protected by the non-woven fabric layer. These tests examined the combination product of fabric and collagen, while Example 3 was just collagen foam. Samples were subjected to burst testing as described above in Examples 2 and 3, using the following parameters:
1. Sample had a weight of about 0.030 grams. About 110 μL PBS was added on top of the fabric resulting in 0 burst pressure.
2. Sample had a weight of about 0.029 grams. About 110 μL of PBS was applied to the polyurethane test block as opposed to the fabric surface. The block was 2 inch×2 inch×⅛ inch with a 0.0075 inch punch through the center. The 9/16 inch test piece was placed over the opening to monitor how the sample seals the opening. Once the sample gels via the PBS and the up and down plunger mixing action of the TA, the burst test was then used to see how well the sample seals the 0.0075 inch opening by applying pressure provided by a syringe pump filled with water. A pressure readout is used to monitor the amount of pressure applied when the seal begins to leak. The gel curve was perfectly flat, so about 110 μL PBS was added around the plunger at a pressure of about 120 mm Hg.
3. Sample had a weight of about 0.028 grams. The sample was applied off center to a PU block; it slipped from the center of the PU block, so the test was stopped.
4. Sample had a weight of about 0.023 grams. About 75 μL PBS was applied to a PU block to start, then another 75 μL PBS was applied around the plunger 60 seconds into cycle. Burst occurred at about 870 mm Hg pressure. Adding the secondary volume of PBS around the plunger allowed the liquid to flow down and around the 9/16 inch punch via gravity. Sample #4 was added to a water bath after peeling away from the PU block. It weighed about 59 mg, so there was >150% moisture uptake.
5. Sample had a weight of about 0.022 grams. About 75 μL PBS was added to PU block to start, then another 75 μL around the plunger 60 seconds into cycle. Burst occurred at about 642 mm Hg pressure.
6. Sample had a weight of about 0.027 grams. About 75 μL PBS was added to PU block to start then another 75 μL around plunger 60 seconds into cycle. Burst occurred at about 577 mm Hg pressure.
7. Sample had a weight of about 0.020 grams. About 75 μL PBS was added to PU block to start then another 75 μL around plunger 60 seconds into cycle. Burst occurred at about 645 mm Hg pressure (burst timed at 75 seconds).
8. Sample had a weight of about 0.017 grams. About 75 μL PBS was added to PU block to start then another 75 μL around plunger 60 seconds into cycle. Burst occurred at about 551 mm Hg pressure.

The above data established that the buttresses produced in accordance with the present disclosure had burst values much higher than expected. The non-woven fabric, acting as a support, may be the cause of this increase, as it was clearly much stronger than versions without the fabric. It appeared the gel was seeping through the fabric during the 4 minute gel time part of the test. It effectively made the fabric the center of a gel sandwich. After the 4 minute cycle, the resulting buttress was a fiber reinforced hydrogel. The hemostatic potential of these materials is also evident as the samples more than doubled their starting weight after completion of the burst test.

Example 5

Purified porcine collagen (CPP) was dissolved in deionized water so that it was at a concentration of about 1% by weight. The pH was adjusted with about 1 N sodium hydroxide and 4-Morpholinepropanesulfonic acid (MOPS) to reach a pH of about 7. The CPP solution was added to a 20 cc syringe. A 4-armed polyethylene glycol having a molecular weight of about 2000 Daltons, functionalized with succinimidyl glutarate groups, (4 arm 2 k PEG SG) was added to a second 20 cc syringe in solution, with the 4 arm 2 k PEG SG. The contents of the two syringes were expelled simultaneously and blended together by a luer assembly connected to the two syringes.

The blended solution was poured into a dish. The NHS ester reacted with the primary amine from the lysine groups on the CPP, thereby forming a stable amide bond. The contents of the dish were then lyophilized, resulting in a thin foam.

A trilysine solution was then added to the foam in order for the stabilized cross linked collagen to absorb the multi-arm amine. The materials were then subjected to a second lyophilization cycle, resulting in a dry foam product.

After the second lyophilization, an additional electrophilic material was added to the dry product. Here, a film formed of an 8-armed polyethylene glycol having a molecular weight of about 15000 Daltons, functionalized with succinimidyl succinate groups, (8 arm 15 k PEG SS), was applied as a film to the dry foam product.

Example 6

Additional collagen foams were produced following the general synthesis described above in Example 1.

About 0.61 grams of CPP was placed in a vacuum oven overnight. This was done to get an accurate weight of the collagen. The following day, the CPP weighed about 0.543 grams (at about 11% water). About 50.33 grams of ultrapure water passed through an analytical lab alter system to and introduced into a tared beaker having the CPP therein. The beaker was placed in a water bath at a temperature of about 34° C. and mixed with a stir bar at 500 rpm. After about 1 hour, the solution was clear and about 1.25 grams of water had evaporated. This was now a 1.10% w/v solution.

About 86 mg trilysine was then added to the beaker. The trilysine was slightly acidic and the pH of the solution rose to about 4.08. About 0.46 grams of 1 N NaOH solution was then added to increase the pH to about 6.08.

About 57.1 mg of MOPS buffer was then added to the beaker and the pH fell to about 5.84. The MOPS concentration was approximately 80 millimolar.

Another 0.26 gram aliquot of 1 N NaOH (total 0.72 grams) was added to adjust the solution to near the target pH of 7.

About 31.3 mg of glycerol was added to the beaker. The components ere blended together for about 5 minutes resulting in a final pH of about 7.04.

About 16.83 grams of the resulting solution was added to a 82.5 cm$^2$ flat PTFE square dish. The dish was left on a level countertop for about 20 minutes to allow the solution to cool and thicken, and then placed in a lyophilizer. The next day, after a 20 hour lyophilization cycle, a foam piece weighing about 0.280 grams fas removed from the dish.

Example 7

The edges of the foam piece produced in Example 6 were trimmed and the foam was placed in a dry box with nitrogen flow to further dry for about 2 days. The foam piece was about 49.125 cm$^2$ in size.

A thin PEG film was prepared by adding about 0.67 grams of an 8-armed polyethylene glycol having a molecular weight of about 15000 Daltons, functionalized with succinimidyl succinate groups (8 arm 15 k PEG SS) was melted on a piece of release paper with a hot plate. A Mylar sheet was placed over the PEG and a roller was used to make a very thin film of PEG. The PEG film was placed in a dry box overnight.

The following day, the release paper was removed from the PEG leaving all the PEG on the Mylar sheet. The PEG on the Mylar sheet was gently warmed on the hotplate. The foam piece from Example 6, which had undergone additional drying under nitrogen flow, was placed on the warm PEG. The side that was facing the PTFE dish during lyophilization was the side placed onto the PEG. The parts were sandwiched between 2 thin polytetrafluoroethylene (PTFE) sheets and rolled with a roller.

The resulting product was returned to the dry box. The Mylar sheet was removed from the structure after a weekend (about 68-72 hours) in the dry box under nitrogen flow, resulting in PEG transfer.

A gel time test vas performed with the TA.XT Plus Texture Analyzer (TA) described above in Example 2.

A polyurethane foam block was placed on the TA setup with the stage kept at a constant temperature of 37° C. Samples were cut from the CPP foams using a ½" punch and placed on the foam block with the PEG side facing down. The test was started and 80 μL of pH 7.4 phosphate buffer solution was added before the TA probe reached the sample.

The TA program measured the distance that the probe moved as it oscillated between the sample height and a set return height, applying a constant force setting. Variations in this distance were seen as the sample began to form a cross linked system h the crosslinking giving the gel its structure. The gel time was determined, with the fastest ent in the reaction mechanism occurring at approximately 130 seconds.

The gelled sample on the foam block was then moved to the burst sensor setup and rested upon a rubber square. The CPP seal covered a 0.025" diameter circular opening on the center of the polyurethane block. A metal top was then placed on top of the block to create a closed system. The syringe pump pumped fluid into the system at a constant flow rate. A pressure meter monitored the system ntil the seal created by the CPP scaffold began to leak. A total of 18 samples were tested for gel time and burst.

The results are summarized below in Table 1.

TABLE 1

| Sample | Weight (g) | Thickness (mm) | Gel Time (sec) | Burst Force (mmHg) | Burst Time (sec) |
|---|---|---|---|---|---|
| 1 | 0.0133 | 0.451 | 152.6 | 478.8 | 72.3 |
| 2 | 0.0155 | 0.488 | TA was stopped too early to collect data - transition was occurring | | |

TABLE 1-continued

| Sample | Weight (g) | Thickness (mm) | Gel Time (sec) | Burst Force (mmHg) | Burst Time (sec) |
|---|---|---|---|---|---|
| 3 | 0.0149 | 0.448 | 217.93 | 95.1 | 22.04 |
| 4 | 0.0133 | 0.426 | 148.29 | sample stuck to probe and leaked as it was pulled from block | |
| 5 | 0.0121 | 0.389 | 209.21 | 114.4 | 38.77 |
| 6 | 0.0143 | 0.46 | 158.63 | 154 | 32.36 |
| 7 | 0.0148 | 0.457 | 241.6 | 134 | 39.42 |
| 8 | 0.0182 | 0.486 | 197.11 | 131.7 | 41 |
| 9 | 0.0141 | 0.42 | 166.68 | 309.5 | 53.3 |
| 10 | 0.0133 | 0.367 | 118.4 | 191.2 | 27.68 |
| 11 | 0.0107 | 0.429 | 119.07 | 133.7 | 22.61 |
| 12 | 0.015 | 0.462 | 239.8 | 552.8 | 63.04 |
| 13 | 0.0169 | 0.468 | 366.5 | 111.4 | 16.35 |
| 14 | 0.0121 | 0.39 | 157.48 | 116.2 | 14.93 |
| 15 | 0.0121 | 0.335 | 119.55 | 165 | 22.29 |
| 16 | 0.0138 | 0.45 | 125.3 | 254.6 | 36.2 |
| 17 | 0..0131 | 0.449 | 142.91 | 170.1 | 24.58 |
| 18 | 0.0144 | 0.429 | 170.13 | 276.1 | 33.74 |
| 19 | 0.0125 | 0.352 | 101.42 | 169 | 24.84 |
| Average | 0.0139 | 0.4293 | 175.1 | 209.2 | 34.4 |
| Standard Deviation | 0.0018 | 0.0438 | 63.7 | 130.7 | 16.0 |

The stoichiometric balance of NHS groups as compared to amines was estimated. The primary amines were only accounted for by the trilysine since an estimate of the contribution of primary amines on the CPP was not evaluated.

The gel time and burst data showed that despite a product with a thickness average of only 0.43 m: the resulting product was effective with bench scale testing. The hydrogel network formed by the crosslinking of PEG-NHS groups and amines had a burst strength average of approximately 200 mm Hg. A multi-arm polyethylene glycol ester with NHS end caps had the ability to react with a primary amine at a physiological pH within a collagen foam scaffold to become an in-situ forming sealing network.

By incorporating trilysine into the foam scaffold and coating with a film of a multi-arm polyethylene glycol ester with NHS end caps (PEG-NHS), a sealing mechanism was created. The ester linkage to the PEG enabled the degradation of this network. The mechanism also acted to stabilize the otherwise water soluble collagen foam. This may be used to enhance the hemostatic and sealing characteristics of a non-woven buttress formed of these materials.

Example 8

A hernia patch of the present disclosure was prepared as follows. A 1.1% CPP in purified water solution was prepared by mixing at about 34° C. for approximately 2 hours. After the collagen was solubilized, trilysine acetate, MOPS buffer salt, and glycerol were blended into the solution while mixing at about 34° C. The solution was pH adjusted to physiological pH with 1N sodium hydroxide in a two-step process. The solution components (% solids) were as follows:

Collagen: 67%
Trilysine acetate: 9%
4-Morpholinepropanesulfonic acid sodium salt (MOPS): 10%
1.0 Normal Sodium Hydroxide: 4%
Glycerol: 10%

A thin layer of the solution was then applied to the textile side of a pre-soaked composite mesh via pipette. After the solution gelled with cooling, the coated mesh was lyophilized. The lyophilization process created a thin and flexible collagen foam embedded in the textile while still maintaining the integrity of the existing adhesion barrier on the composite mesh. The coated composite mesh was dried under nitrogen overnight to remove residual water. A thin layer of reactive 8-arm succinimidyl succinate polyethylene glycol (15,000 Daltons) was applied via hot melt lamination to foam a coating on the composite mesh.

The coated composite mesh was subjected to functional testing using a 5965 Dual Column Universal Testing System available from Instron, operating in the shear mode. In this test protocol, the mesh was activated with saline solution and applied to a collagen film before incubation at about 37° C. for about 5 minutes. The sample was then loaded into the test fixture and the shear force was measured at a constant rate of about 0.42 mm/second. The results are summarized below in Table 2.

TABLE 2

| Sample | Maximum Load (N/cm$^2$) |
|---|---|
| 1 | 8.65 |
| 2 | 12.52 |
| 3 | 12.67 |
| 4 | 9.31 |
| 5 | 13.34 |
| 6 | 12.96 |
| 7 | 12.34 |
| 8 | 13.35 |
| 9 | 11.77 |
| 10 | 12.55 |
| 11 | 10.76 |
| 12 | 11.37 |
| Average Force | 11.80 |
| Standard Deviation | 1.53 |

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A medical device comprising:
   a fibrous substrate; and
   a foam body comprising the reaction product of a nucleophilic precursor component and an electrophilic precursor component;
   wherein the foam body includes an additional nucleophile for stabilization, and
   wherein the medical device is an implant having a thickness from about 0.1 mm to about 3 mm, and the implant has a film including an electrophilic material on a surface thereof.

2. The medical device of claim 1, wherein the fibrous substrate is selected from the group consisting of knitted structures, woven structures, non-woven structures, and combinations thereof.

3. The medical device of claim 1, wherein the fibrous substrate comprises a polymer selected from poly(lactic acid), poly(glycolic acid) poly(trimethylene carbonate), poly(dioxanone), poly(hydroxybutyrate), poly(phosphazine), polyethylene terephthalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, poly (saccharides), polyamides, poly (iminocarbonates), polyalkylene oxalates, polyoxaesters, polyorthoesters, polyphosphazenes, or biopolymers.

4. The medical device of claim 1, wherein the fibrous substrate comprises oxidized cellulose.

5. The medical device of claim 1, wherein the fibrous substrate possesses pores.

6. The medical device of claim 5, wherein the fibrous substrate has an effective porosity from about 3% to about 72%.

7. The medical device of claim 1, wherein the nucleophilic precursor component is selected from the group consisting of collagen, trilysine, and combinations thereof.

8. The medical device of claim 1, wherein the electrophilic precursor component comprises a multi-arm polyethylene glycol functionalized with N-hydroxysuccinimide groups.

9. The medical device of claim 1, wherein the medical device is selected from the group consisting of surgical buttresses, hernia patches, and tissue scaffolds.

10. The medical device of claim 1, wherein the medical device is a surgical buttress having a thickness from about 0.1 mm to about 0.5 mm.

11. The medical device of claim 1, wherein the medical device is a buttress having a thickness from about 0.2 mm to about 0.4 mm.

12. The medical device of claim 1, wherein the medical device is a hernia patch having a thickness from about 0.3 mm to about 2.5 mm.

13. A medical device comprising:
a fibrous substrate; and
a foam body consisting essentially of the reaction product of a nucleophilic precursor component and an electrophilic precursor component;
wherein the foam body includes an additional nucleophile for stabilization, and
wherein the medical device is an implant having a thickness from about 0.1 mm to about 3 mm, and the implant has a film including an electrophilic material on a surface thereof.

* * * * *